United States Patent
Fenech

(10) Patent No.: US 10,881,385 B2
(45) Date of Patent: Jan. 5, 2021

(54) RADIAL TELESCOPING GUIDE APPARATUS FOR DELIVERY OF A FLEXIBLE INSTRUMENT AND METHODS OF USE

(71) Applicant: INTUITIVE SURGICAL OPERATIONS, INC., Sunnyvale, CA (US)

(72) Inventor: Carolyn M. Fenech, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 360 days.

(21) Appl. No.: 15/697,879

(22) Filed: Sep. 7, 2017

(65) Prior Publication Data
US 2018/0070935 A1    Mar. 15, 2018

Related U.S. Application Data

(60) Provisional application No. 62/393,786, filed on Sep. 13, 2016.

(51) Int. Cl.
*A61B 17/00*   (2006.01)
*A61B 34/30*   (2016.01)
*A61B 34/00*   (2016.01)

(52) U.S. Cl.
CPC ........ *A61B 17/00234* (2013.01); *A61B 34/30* (2016.02); *A61B 34/77* (2016.02);
(Continued)

(58) Field of Classification Search
None
See application file for complete search history.

(56) References Cited

U.S. PATENT DOCUMENTS

| 6,331,181 B1 | 12/2001 | Tierney et al. |
| 6,380,732 B1 | 4/2002 | Gilboa |

(Continued)

OTHER PUBLICATIONS

Telescopic. (n.d.). In YourDictionary. Retrieved from https://www.yourdictionary.com/Telescopic May 5, 2020.*

(Continued)

*Primary Examiner* — Thomas McEvoy
(74) *Attorney, Agent, or Firm* — Haynes and Boone, LLP

(57) ABSTRACT

Described herein is an apparatus for guiding an elongated flexible instrument, the apparatus comprising a telescoping support assembly including a plurality of support members extending along a longitudinal axis between a proximal end and a distal end. Each of the support members comprises a ring having an inner surface, an outer surface, and at least one flange. Each flange extends from the inner surface of the ring to define a central passageway extending along the longitudinal axis and having a substantially constant width, which is configured to receive the elongated flexible instrument. The assembly is configured to selectively transition from a compressed to an expanded configuration along the longitudinal axis while each support member is interlocked with at least one other support member, and is adapted to support the elongated flexible instrument as the instrument is advanced along the longitudinal axis.

22 Claims, 15 Drawing Sheets

(52) U.S. Cl.
    CPC ............ *A61B 2017/00305* (2013.01); *A61B 2017/00469* (2013.01); *A61B 2017/00991* (2013.01); *A61B 2034/301* (2016.02)

(56) References Cited

U.S. PATENT DOCUMENTS

| | | |
|---|---|---|
| 6,389,187 B1 | 5/2002 | Greenaway et al. |
| 6,491,701 B2 | 12/2002 | Tierney et al. |
| 7,316,681 B2 | 1/2008 | Madhani et al. |
| 7,772,541 B2 | 8/2010 | Froggatt et al. |
| 8,672,880 B2 | 3/2014 | Cohen et al. |
| 8,900,131 B2 | 12/2014 | Chopra et al. |
| 8,961,533 B2 | 2/2015 | Stahler et al. |
| 9,259,274 B2 | 2/2016 | Prisco |
| 9,452,276 B2 | 9/2016 | Duindam et al. |
| 2008/0287951 A1* | 11/2008 | Stoneburner .......... A61B 5/107 606/63 |
| 2013/0239490 A1* | 9/2013 | Peng .................... F16M 11/28 52/111 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

RADIAL TELESCOPING GUIDE APPARATUS FOR DELIVERY OF A FLEXIBLE INSTRUMENT AND METHODS OF USE

PRIORITY INFORMATION

This application is a non-provisional application claiming priority to U.S. Provisional Application No. 62/393,786, filed Sep. 13, 2016, the disclosure of which is incorporated herein by reference in its entirety.

FIELD

The present disclosure is directed to systems and methods for navigating a patient anatomy to conduct a minimally invasive procedure, and more particularly to apparatus and methods for guiding and supporting the delivery of a flexible interventional instrument into a patient anatomy.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. To reach the target tissue location, a minimally invasive interventional instrument may navigate natural or surgically created passageways in anatomical systems such as the lungs, the colon, the intestines, the kidneys, the heart, the circulatory system, or the like. Control of such an elongate device by medical personnel involves the management of several degrees of freedom including at least the management of insertion and retraction of the elongate device as well as steering of the device. In addition, different modes of operation may also be supported.

Teleoperational interventional systems may be used to insert and guide the flexible interventional instruments into and through the patient anatomy. Several interventional instruments are made of flexible material that allows for maneuverability through a patient's body. In existing systems, at least a portion of the interventional instrument extending between the patient and a teleoperational manipulator is unsupported, and the flexible nature of the instrument can cause it to bend, twist, or buckle in an undesirable manner at a point external to the patient's body when force is exerted to insert the instrument into the patient's anatomy. Deformation of the instrument may damage internal components such as optical fiber shape sensors or endoscopic equipment.

Improved systems and methods are needed for guiding and supporting interventional instruments as they are inserted into a patient anatomy to prevent instrument deformation.

SUMMARY

The embodiments of the invention are summarized by the claims that follow the description.

Consistent with some embodiments, the present disclosure describes an apparatus for guiding an elongated flexible instrument, the apparatus comprising a telescoping support assembly including a plurality of support members extending along a longitudinal axis between a proximal end and a distal end. In one aspect, each of the support members comprises a ring having an inner surface, an outer surface, and a plurality of flanges. Each of the plurality of flanges extends from the inner surface of the ring to define a central passageway, which is configured to receive the elongated flexible instrument. The assembly is configured to selectively transition from a compressed to an expanded configuration along the longitudinal axis, and is adapted to support the elongated flexible instrument as the instrument is advanced along the longitudinal axis.

In one aspect, each of the plurality of flanges of each of the plurality of support members extends at a perpendicular angle from the inner surface of the ring toward a radial center of the support member.

In one aspect, the plurality of flanges of each support member comprises elongate wedges extending from the inner surface of the ring.

In one aspect, each of the elongate wedges taper from a wide base at the inner surface of the ring to a narrow flange tip defining a circumferential boundary of the central passageway.

In one aspect, each of the plurality of support members is radially offset from one another such that the plurality of flanges of each support member can nest into each adjacent support member.

Consistent with some embodiments, the present disclosure describes an apparatus for guiding an elongated flexible instrument, the apparatus comprising a telescoping support assembly including a proximal end, a distal end, and a plurality of support members extending along a longitudinal axis between the proximal end and the distal end. Each of the plurality of support members comprises a ring having an inner surface, an outer surface, and at least one flange extending perpendicularly from the inner surface of the ring to define a central passageway, which is configured to receive the elongated flexible instrument. The telescoping support assembly is configured to selectively transition from a compressed configuration to an expanded configuration along the longitudinal axis, and is adapted to support the elongated flexible instrument as the elongated flexible instrument is advanced along the longitudinal axis.

In one aspect, the at least one flange of each support member comprises an elongate wedge tapering from the inner surface of the ring into a flange tip.

In one aspect, the flange tip defines a circumferential boundary of the central passageway.

In one aspect, the at least one flange of each centrally disposed support member is configured to contact the at least one flange of the proximally adjacent support member and the at least one flange of the distally adjacent support member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 1:
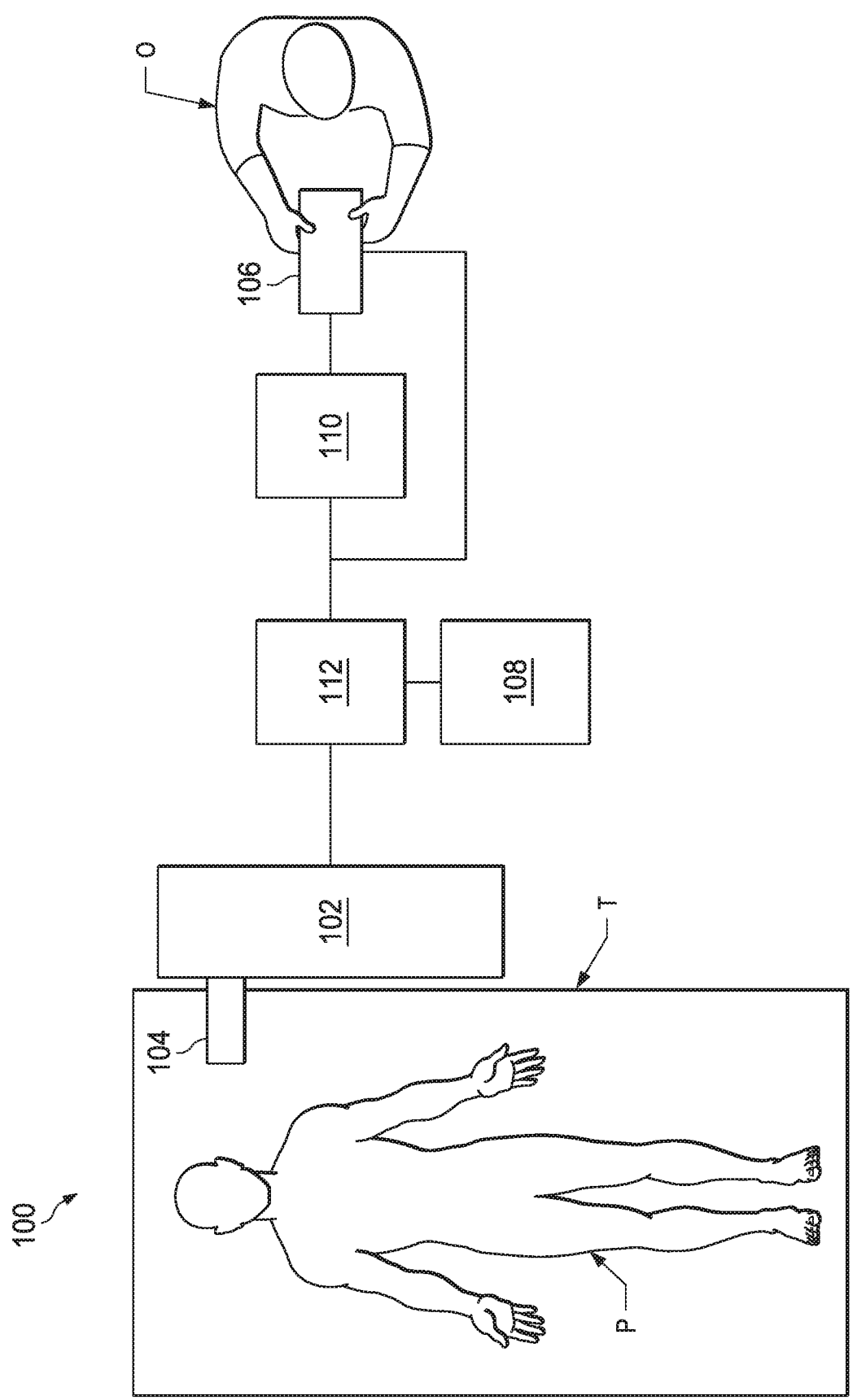
FIG. 1 is a simplified diagram of a teleoperated medical system in accordance with embodiments of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

The teleoperational assembly 102 supports the medical instrument system 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the operator O. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the operator input system 106 may be oriented so the operator O can control the medical instrument system 104 and the operator input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments, often for purposes of imaged guided surgical procedures, the display system 110 may display a virtual navigational image in which the actual location of the medical instrument 104 is registered (i.e., dynamically referenced) with the preoperative or concurrent images/model to present the operator O with a virtual image of the internal surgical site from the viewpoint of the location of the tip of the instrument 104. In some examples, the viewpoint may be from a tip of medical instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display system 110 may display a virtual navigational image in which the actual location of the medical instrument is registered with preoperative or concurrent images to present the operator O with a virtual image of medical instrument within the surgical site from an external viewpoint. An image of a portion of the medical instrument or other graphical or alphanumeric indicators may be superimposed on the virtual image to assist the surgeon controlling the instrument 104. As described herein, visual representations of data points may be rendered to the display system 110. For example, measured data points, moved data points, registered data points, and other data points described herein may be displayed on the display system 110 in a visual representation. The data points may be visually represented in a user interface by a plurality of points or dots on the display or as a rendered model, such as a mesh or wire model created based on the set of data points. In some embodiments, a visual representation may be refreshed in the display system 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a non-transitory machine-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, another portion of the processing being performed at master assembly 106, and the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

The control system 112 may further include a virtual visualization system to provide navigation assistance to operator O when controlling the medical instrument system(s) 104 during an image-guided surgical procedure. Virtual navigation using the virtual visualization system is based upon reference to the acquired preoperative or intra-operative dataset of the anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software, which may be used in combination with manual inputs is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the anatomy of patient P. The location can be used to produce both macro-level (external) tracking images of the anatomy of patient P and virtual internal images of the anatomy of patient P. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In some embodiments, the teleoperational system may include more than one teleoperational assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2:
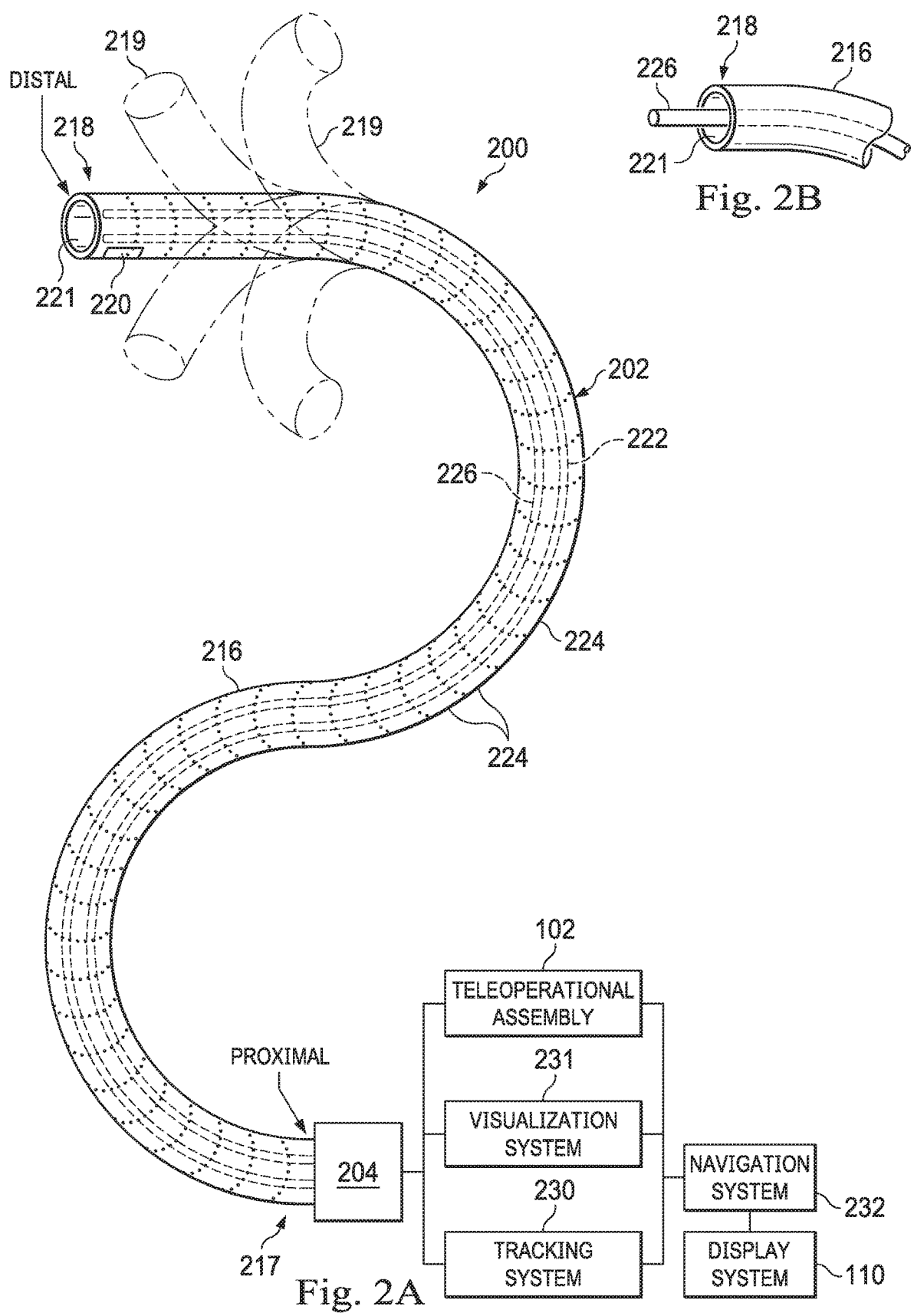
FIG. 2A is a simplified diagram of a medical instrument system according to some embodiments of the present disclosure.
FIG. 2B is a simplified diagram of a medical instrument with an extended medical tool according to some embodiments of the present disclosure.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

The instrument system 200 includes an elongate device 202 (e.g., a catheter system) coupled to a drive unit 204. The elongate device 202 includes an elongated flexible body 216 having a proximal end 217 and a distal end or tip portion 218. In one embodiment, the flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

When using a teleoperational assembly to insert a catheter (or other elongate, flexible medical instrument) into a patient anatomy, the outstretched catheter should be supported as it is advanced into the patient. Otherwise, as the catheter is pushed from a proximal end and encounters friction in the patient anatomy at the distal end, the catheter may buckle or bend. To prevent this deformation of the catheter, an instrument guiding apparatus may be used to provide support to the catheter at regular intervals as it enters the patient anatomy along an insertion axis. In some instances, the catheter is threaded through a central channel of the instrument guiding apparatus before the catheter is introduced into the patient's anatomy. In the embodiments described herein, the instrument guiding apparatus can transition between a compressed configuration and an expanded configuration, allowing the instrument guiding apparatus to laterally support the catheter along its changing external length as it is manipulated into and out of the patient anatomy.

In embodiments described herein, the instrument guiding apparatus includes multiple telescoping support members that maintain the catheter's alignment along the insertion axis as it transitions between a compressed configuration and an expanded configuration. Generally, the catheter is introduced into the guiding apparatus while the apparatus is in a compressed configuration. After a distal portion of the catheter is threaded through all of the nested support members of the guiding apparatus, the guiding apparatus can be expanded about a remaining length of the catheter. The instrument guiding apparatus returns to a compressed or nested configuration as the catheter is advanced into the patient anatomy and the exposed length of the catheter decreases. In some instances, it is desirable to minimize the compressed length of the guiding apparatus to allow for the maximum length of useable (i.e., insertable) catheter length. In some examples of a telescoping guide apparatus such as an apparatus including disc-shaped support members, the supports are generally placed very far apart when the apparatus is fully extended to facilitate collapsing into as short a length as possible. Consequently, the unsupported lengths of the catheter between adjacent discs of the support members may buckle as the guide apparatus expands and the gaps between the passageways of adjacent support members widen. Instead of the discs of each support member supporting the catheter 360 degrees around its circumference for short sections, each support member described herein includes elongated radial flanges configured to support the catheter at different radial points around the circumference of the catheter for longer sections, thereby effectively supporting the catheter along the entire length of the guiding apparatus. Alternatively, the guide apparatus may be configured to allow axial gaps between the supported sections, thereby providing an even more compressed length. Such embodiments may be more useful in procedures utilizing a relatively stiff elongate instrument. The radial flanges may number two or more for each support member, and they may be oriented perpendicular to the insertion axis and at opposing angles relative to each other. The radial flanges nest against each other as the guide apparatus collapses into a compressed configuration, resulting in a desirably short compressed length. As the catheter enters the patient anatomy, the guiding apparatus embodiments described herein provide a suitably short compressed size while minimizing catheter buckling between adjacent support members and providing stable support to the catheter as it journeys into, through, and from the patient anatomy. Thus, the embodiments described herein effectively provide stable support to the catheter as it journeys into, through, and from the patient anatomy.

Figure 3:
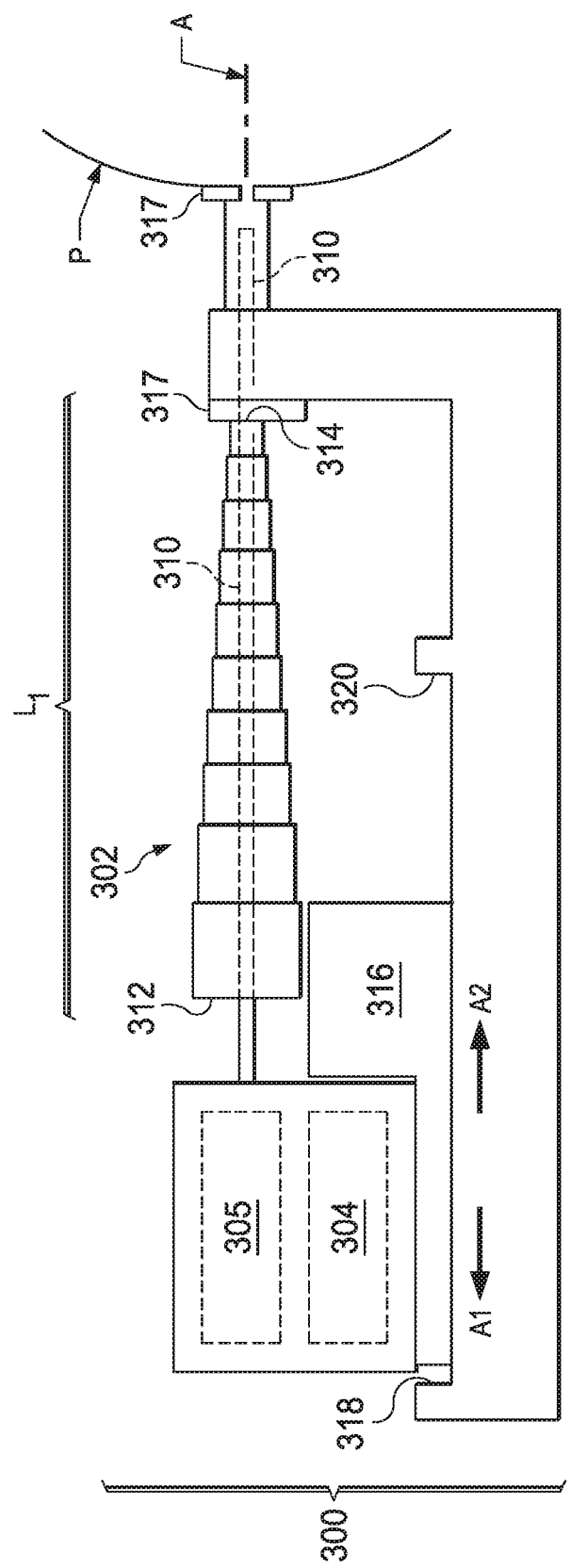
FIG. 3 is a simplified diagram of a side view of a teleoperational manipulator assembly, an elongate instrument, and an exemplary instrument guiding apparatus according to an embodiment of the present invention.

FIG. 3 diagrammatically illustrates an instrument interface portion 300 of a teleoperational manipulator assembly (e.g., teleoperational manipulator assembly 102) and an instrument guiding apparatus 302 according to an embodiment of the present invention. The instrument interface portion 300 includes drive inputs 304 that may provide mechanical coupling of the instrument end effector and flexible body steering mechanism to the drive motors mounted to the teleoperational manipulator. For example, a pair of drive inputs may control the pitch motion of the distal end of the instrument flexible body, with one adaptor of the pair controlling motion in the upward direction and the other of the pair controlling motion in the opposite downward direction. Other pairs of drive inputs may provide opposing motion in other degrees of freedom for the flexible body and/or the end effector. In some embodiments, the drive inputs 304 may be coupled to or positioned within an instrument control unit 305, which controls the positioning of an elongate instrument such as a catheter 310. Instrument interfacing with teleoperational or robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The instrument interface portion 300 may also control instrument insertion by moving linearly along an insertion axis A.

During use, the catheter 310 is positioned within instrument guiding apparatus 302 and the instrument guiding apparatus 302 acts to minimize the buckling of the catheter 310 as the catheter 310 advances toward, remains within, and retracts from the patient anatomy. The instrument guiding apparatus 302 has a proximal end 312 and a distal end 314. In some embodiments, the proximal end 312 of the instrument guiding apparatus 302 is detachably coupled to a mounting plate 316 of the instrument interface portion 300. The mounting plate 316 may be moveable (e.g., along the insertion axis A) relative to a proximal end 318 and a distal end 320 of the instrument interface portion 300. The proximal end 318 and the distal end 320 may or may not be disposed at the physical ends of the instrument interface portion 300. For example, in the pictured embodiment, the proximal end 318 and the distal end 320 comprise motion stops disposed away from the actual ends of the instrument interface portion 300 that are shaped and configured to halt the axial translation of the mounting plate 316. The distal end 314 may be manually or teleoperationally pulled distally along the insertion axis A to expand the guiding apparatus 302. During use, the distal end 314 of the instrument guiding apparatus 302 may be detachably coupled to an anchor 317 within the surgical field. Such an anchor may be positioned on the surgical table, on a surgical frame, or on the patient anatomy. The anchor 317 may be positioned on the instrument interface portion 300 (e.g., on a flexible instrument manipulator or FIM), the surgical table, on a surgical frame, or on the patient anatomy. In one example, the anchor 317 may comprise a mouth guard clamped by patient's teeth. The instrument guiding apparatus 302 provides lateral support along the length of the catheter 310 positioned within the instrument guiding apparatus 302 to minimize buckling of the exposed length of the catheter 310 as it is pushed into and pulled from the patient's body P (e.g., along the insertion axis A, in the directions of arrow A2 and arrow A1 respectively). After the distal end 314 is attached to the anchor 317 and/or coupled to the patient anatomy P, and the catheter 310 is advanced through the instrument guiding apparatus 302 into the patient anatomy P, the instrument control unit 305 advances the proximal end 312 of the instrument guiding apparatus 302 distally, causing the individual support members to telescope into one another and a length L1 of the instrument guiding apparatus 302 to shorten while still supporting the external portions of the catheter 310.

Figure 4:
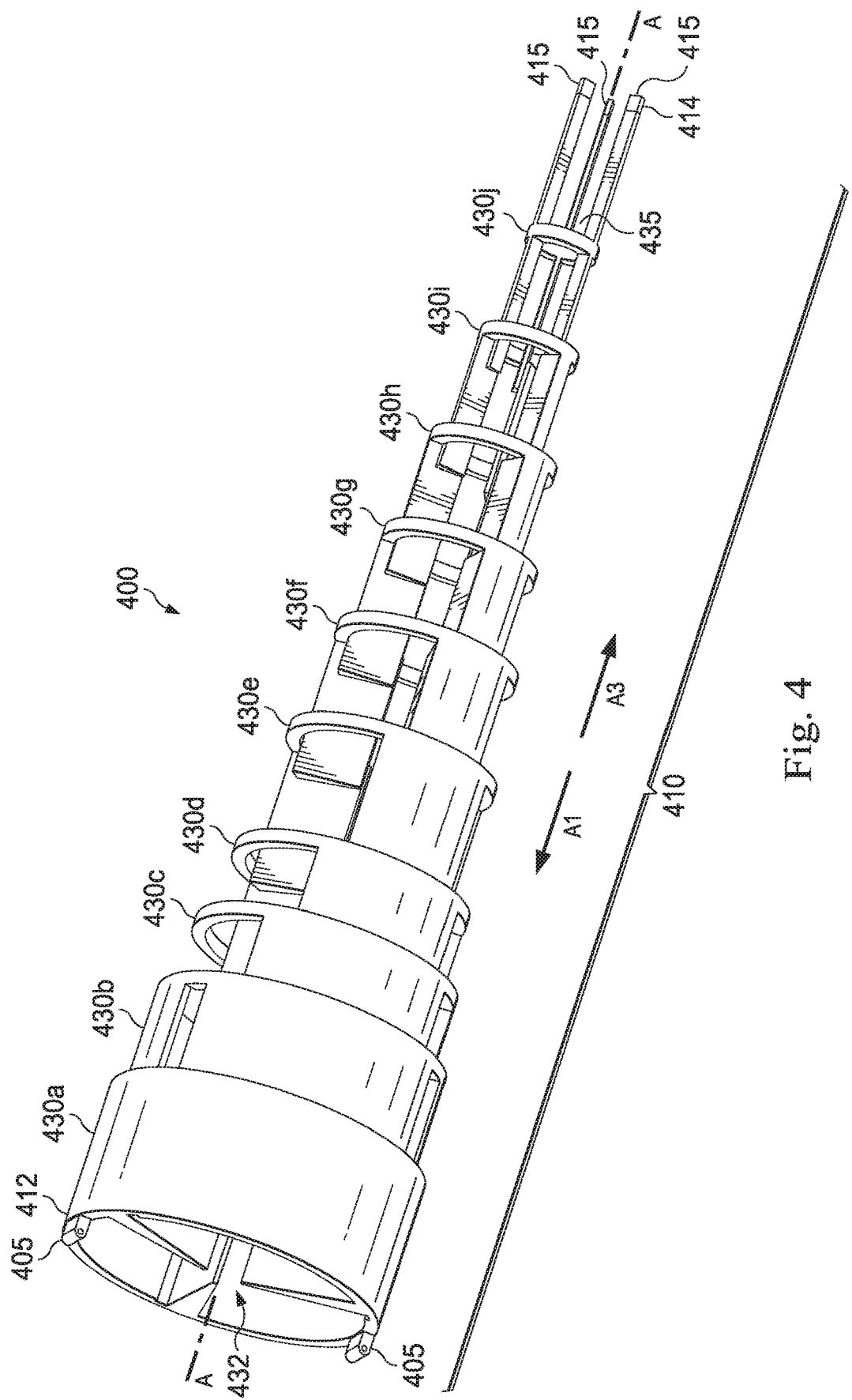
FIG. 4 illustrates a perspective view of the instrument guiding apparatus 400 in an expanded configuration.

FIG. 4 illustrates a perspective view of an instrument guiding apparatus 400 in an almost fully expanded configuration according to one embodiment of the present disclosure. The instrument guiding apparatus 400 is a particular example of the instrument guiding apparatus 302 shown in FIG. 3. The design, function, and use of this specific embodiment are the same as described with reference to the instrument guiding apparatus 302 shown in FIG. 3 unless otherwise noted or apparent from the description. In the pictured embodiment, the instrument guiding apparatus 400 includes optional proximal couplers 405, a telescoping support assembly 410 that extends between a first end 412 to a distal end 414, and an optional distal coupler 415 at the distal end 414.

The proximal coupler 405 may detachably couple the first end 412 of telescoping support assembly to the instrument interface portion 300 (e.g., the mounting plate 316 shown in FIG. 3) and/or the instrument control unit 305. The proximal coupler 405 may include any of a variety of fastening elements capable of securely yet detachably coupling the proximal coupler 405 of the instrument guiding apparatus 400 to the teleoperational manipulator assembly, including, without limitation, snap-fit engagements, frictional engagements, hook-and-eye fasteners, pins, carriage bolts, and mating screws.

During use, the distal coupler 415 may be detachably coupled to an anchor (e.g., anchor 317 shown in FIG. 3) within the surgical field. As mentioned previously, such an anchor or stabilizer may be positioned on the surgical table, on a surgical frame, or on the patient anatomy. The distal coupler 415 may be used to detachably couple the instrument guiding apparatus 400 to the patient or another device (e.g., a stabilizer mounted to the patient or the surgical table) to stabilize the distal end of the instrument guiding apparatus as the catheter 310 is passed through the telescoping support assembly 410. For example, in some embodiments, the distal coupler 415 may be connected to a stabilizer, such as, by way of non-limiting example, a hook or a tether, in the surgical field. During use, the stabilizer may be connected to the patient's body and/or the surgical table. In some instances, the stabilizer may comprise an introducer sheath at the insertion site configured to receive the catheter 310. The instrument guiding apparatus 400 provides support along the length of the catheter 310 between the stabilizer and the proximal coupler 405. In general, the distal coupler 415 is stationary with respect to the patient anatomy P during the procedure.

Figure 11:
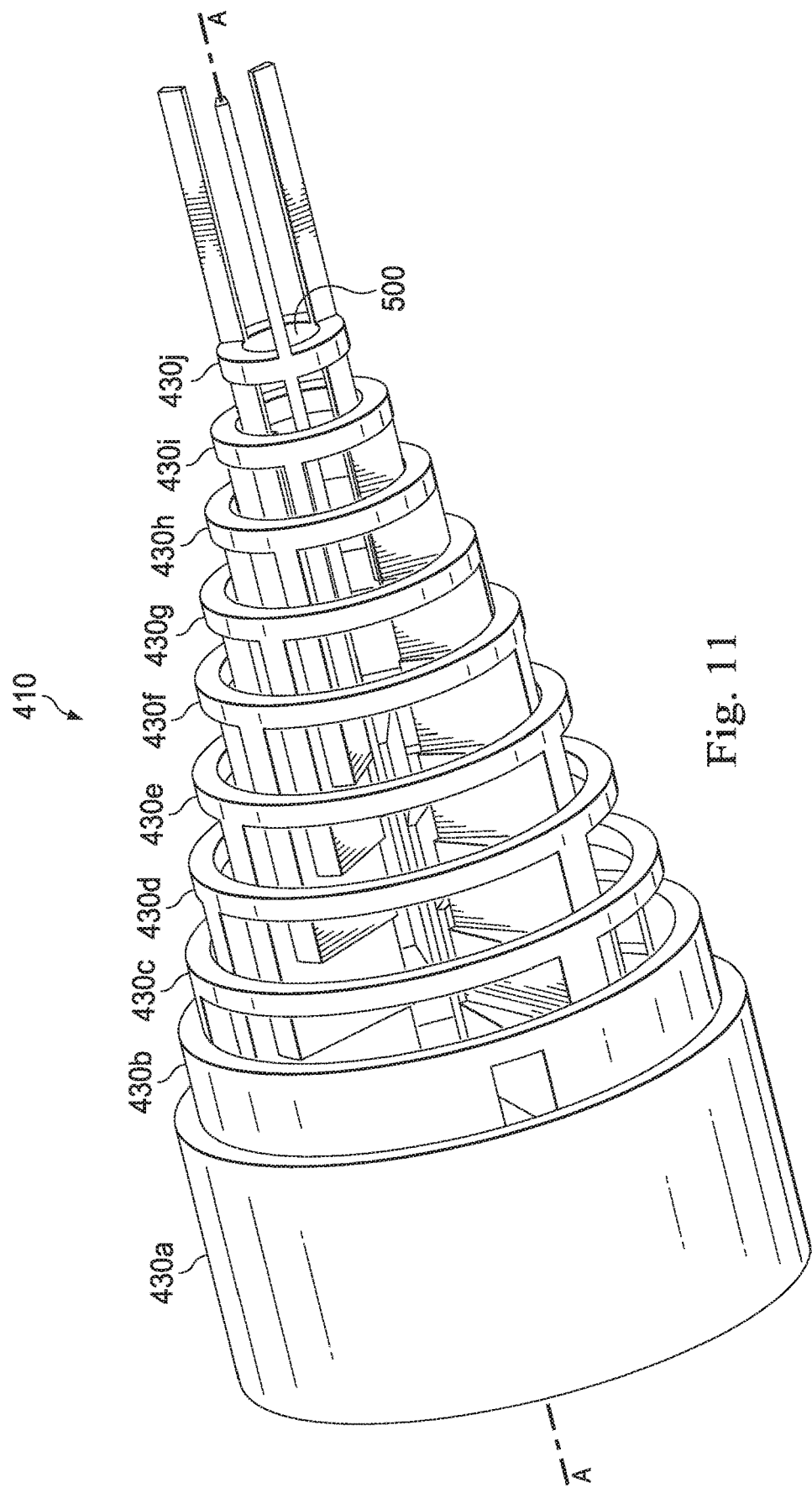
FIG. 11 illustrates another perspective view of the telescoping support assembly shown in FIG. 4 in an expanded configuration.
Figure 12:
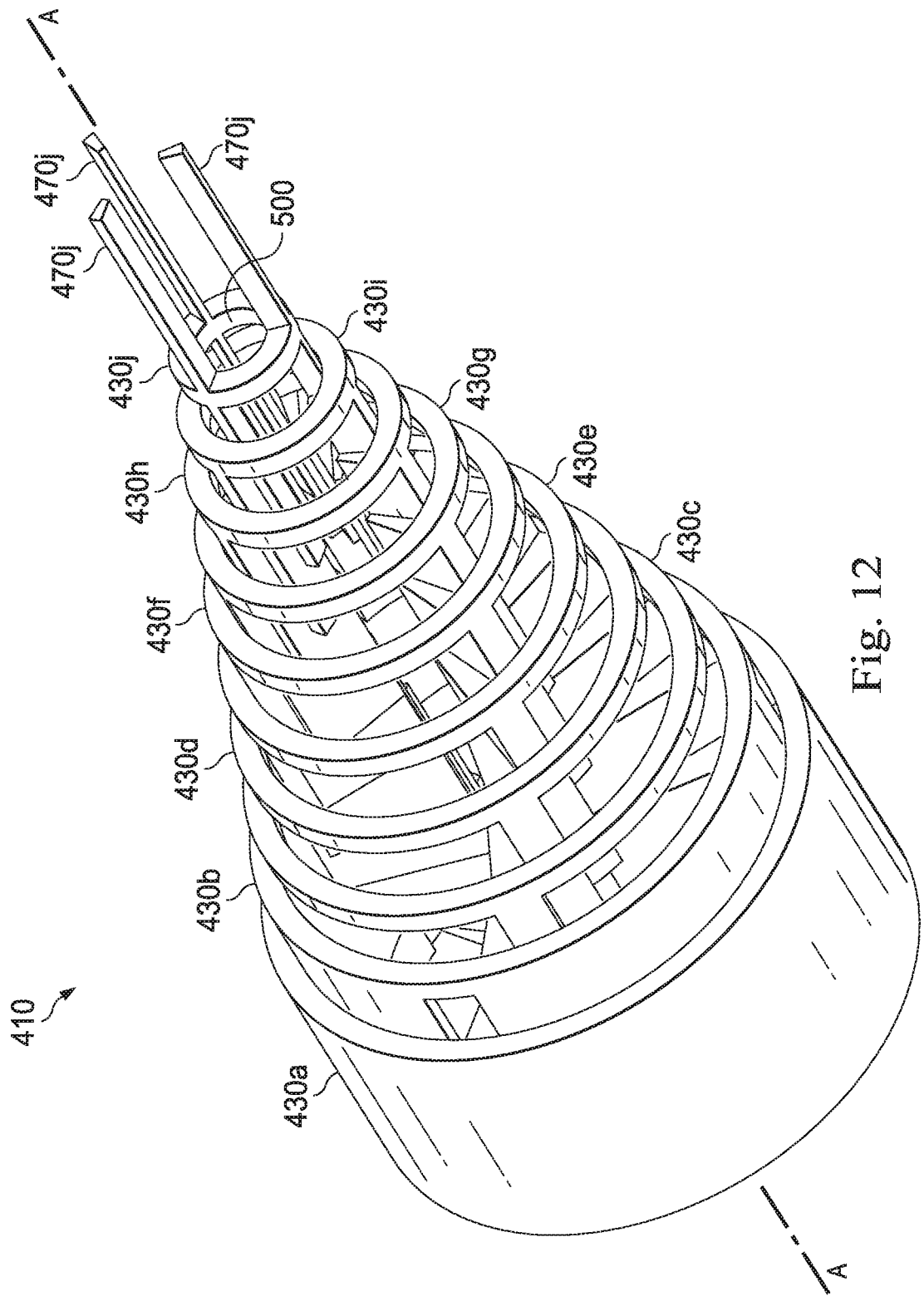
FIG. 12 illustrates another perspective view of the telescoping support assembly shown in FIG. 4 in an expanded configuration.
Figure 13:
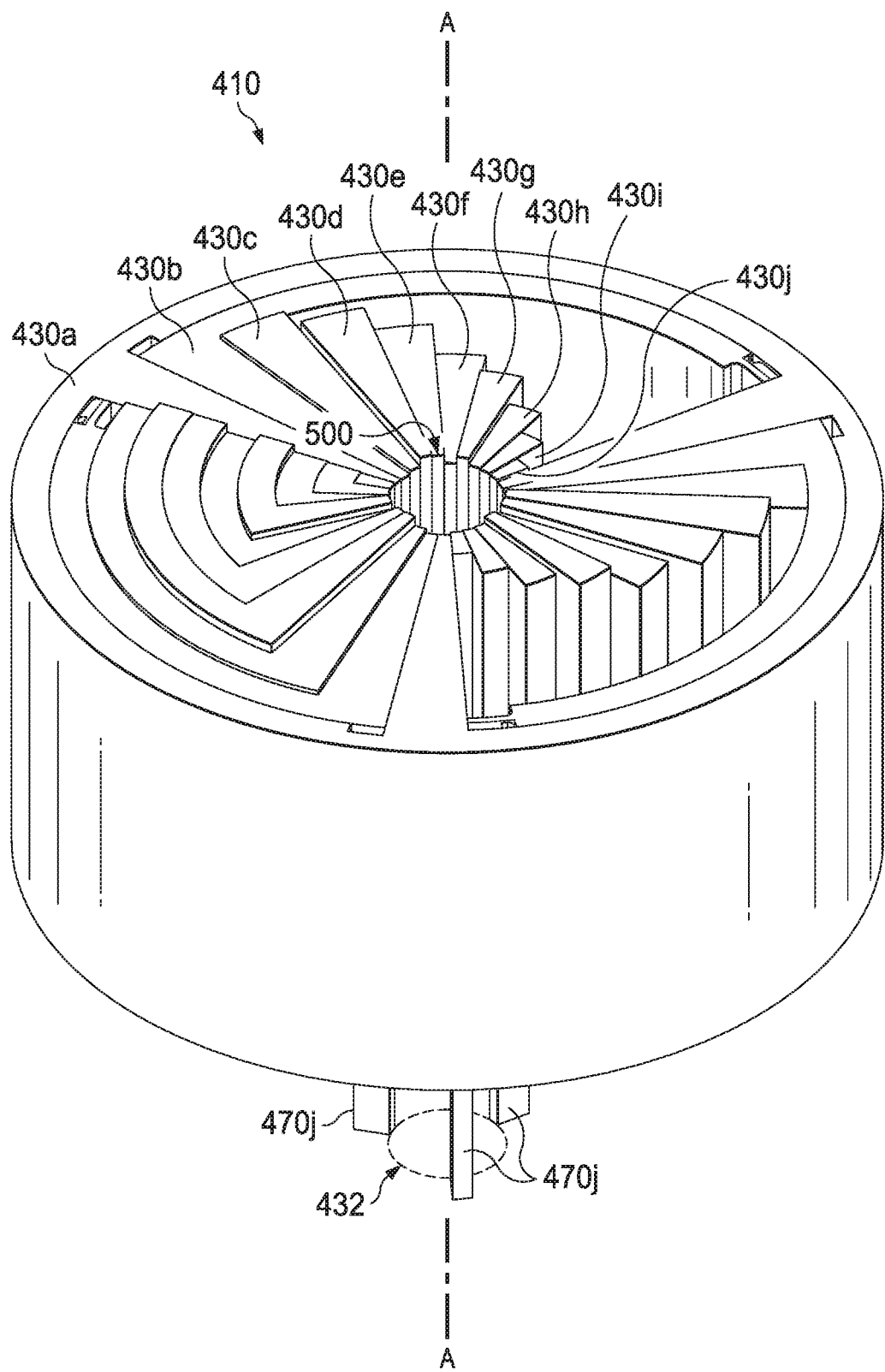
FIG. 13 illustrates a perspective view (from the top) of the telescoping support assembly shown in FIG. 4 in a compressed configuration according to one embodiment of the present disclosure.
Figure 14:
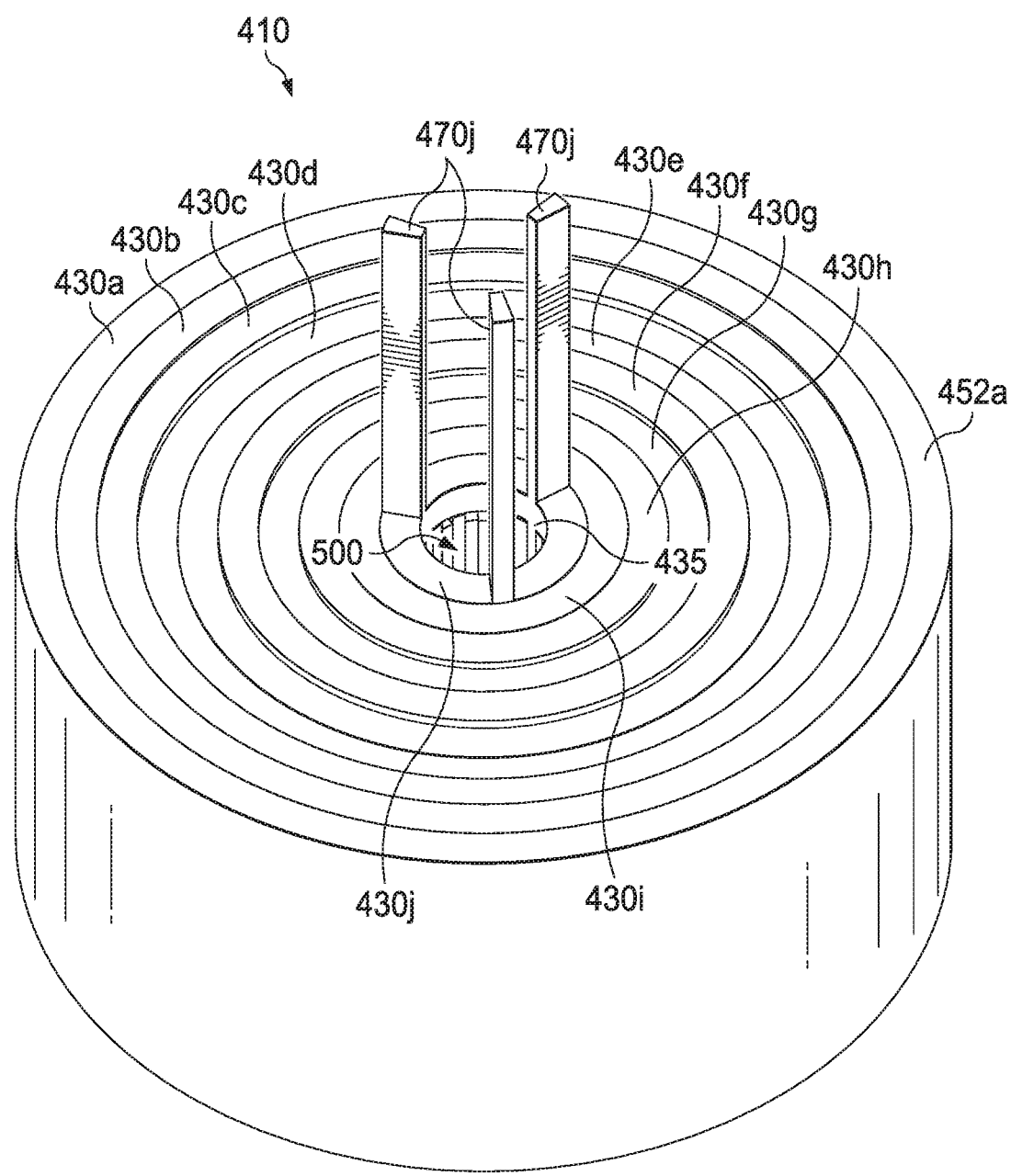
FIG. 14 illustrates a perspective view (from the bottom) of the telescoping support assembly shown in FIG. 4 in a compressed configuration.

The variable-length support assembly 410 can expand from the compressed configuration shown in FIGS. 13 and 14 into the expanded configuration shown in FIGS. 4 and 10-12 as the proximal coupler 405 moves proximally in the direction of arrow A1 along the insertion axis A. In some instances, motion of the catheter 310 in and out of the patient anatomy P is coupled to the motion of the proximal coupler 405. In some instances, the proximal coupler 405 moves in the direction of the arrow A2 in concert with the catheter 310 as the catheter 310 is initially advanced distally along the insertion axis A and into the patient anatomy. Similarly, in some instances, the proximal coupler 405 moves in the direction of the arrow A1 along the insertion axis A in concert with the catheter 310 as the catheter 310 is removed from the patient anatomy. The variable-length support assembly 410 may collapse or telescope into a compressed configuration as the instrument interface portion 300 and/or the instrument control unit 305 shown in FIG. 3 advances the catheter 310 further into the patient anatomy, thereby linearly displacing the variable-length support assembly 410 in the direction of arrow A2 (and arrow A3 shown in FIG. 4) along the axis A. When the catheter 310 is fully inserted into the patient, the variable-length support assembly 410 is in a compressed condition as illustrated in FIGS. 13 and 14. When the catheter 310 is only partially inserted into the patient, the variable-length support assembly 410 is partially extended as shown in FIGS. 4 and 10-12. When the catheter 310 is fully withdrawn from the patient or at least retracted (e.g., into a delivery instrument) out of direct contact with patient anatomy, the variable-length support assembly 410 is fully extended.

As shown in FIG. 4, the telescoping support assembly 410 is disposed between the proximal coupler 405 and the distal coupler 415. As shown in FIGS. 4 and 10-15, the telescoping support assembly 410 includes multiple support members 430 connected to each other to create a selectively expandable scaffolding structure. In the pictured embodiment, the telescoping support assembly 410 includes ten support members 430a-j that are coupled to each other to create a selectively expandable support frame assembled in a telescoping configuration. Other embodiments can have more or less support members. In particular, each support member 430 is shaped and configured to nest into the proximally adjacent support member 430. For example, the distal-most support member 430j nests into the proximal adjacent support member 430i, the support member 430i nests into the support member 430h, the support member 430h nests into the support member 430g, the support member 430g nests into the support member 430f, the support member 430f nests into the support member 430e, the support member 430e nests into the support member 430d, the support member 430d nests into the support member 430c, the support member 430c nests into the support member 430b, the support member 430b nests into the support member 430a. In the pictured embodiment, all the support members 430 have a generally cylindrical profile. Other shapes, however, are contemplated for the support members 430, including without limitation, cuboid, ovoid, and rhomboid shapes. In the pictured embodiment, the proximal-most support member 430a and the distal-most support member 430j are uniquely shaped, while the central support members 430b-i are more similar in shape.

In use, the catheter 310 may be threaded through a proximal aperture 432 of the proximal-most support member 430a of the telescoping support assembly 410, through each of the support members 430 (e.g., while the support members 430 are nested together in a compressed configuration), and through a distal aperture 435. In some embodiments, the proximal aperture 432 is linearly aligned with the distal aperture 435 along the insertion axis A. The telescoping support assembly 410 can shift from the compressed configuration shown in FIGS. 13 and 14 into the expanded configuration shown in FIGS. 4 and 10-12 as the catheter 310 is advanced distally toward the patient along the insertion axis A. As shown in FIG. 4, when the telescoping support assembly 410 is in an expanded configuration, each support member 430 extends distally from its immediately proximal support member. As the instrument interface portion 300 and/or the instrument control unit 305 shown in FIG. 3 advances the catheter 310 into the patient anatomy, and applies a linear force to the telescoping support assembly 410 in the direction of arrow A2 along the insertion axis A (or arrow A3 in FIG. 4), the telescoping support assembly 410 collapses or telescopes into a compressed configuration.

Figure 5A:
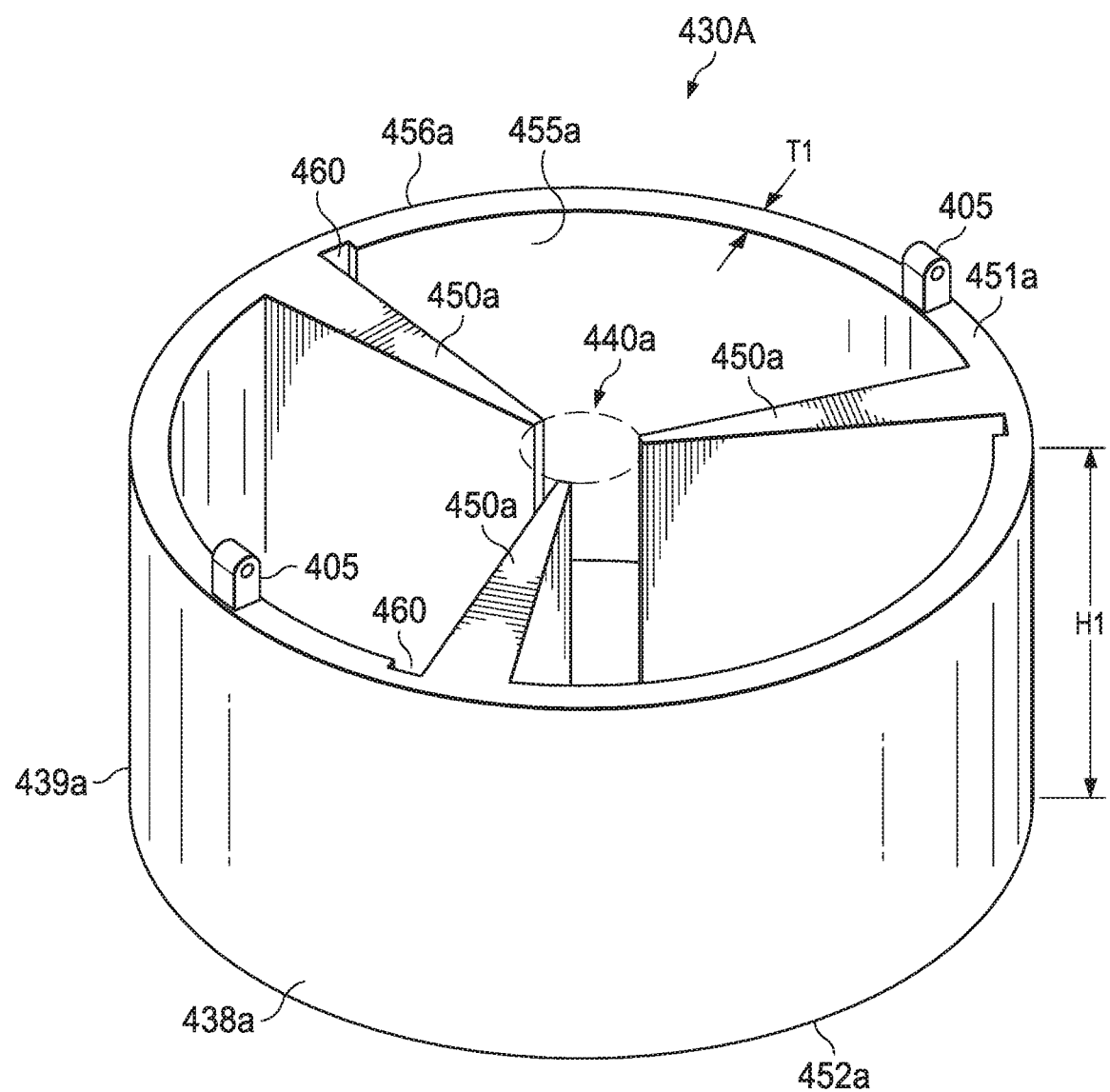
FIG. 5A illustrates a perspective view of an exemplary support member of the instrument guiding apparatus shown in FIG. 4 according to one embodiment of the present disclosure.
Figure 5B:
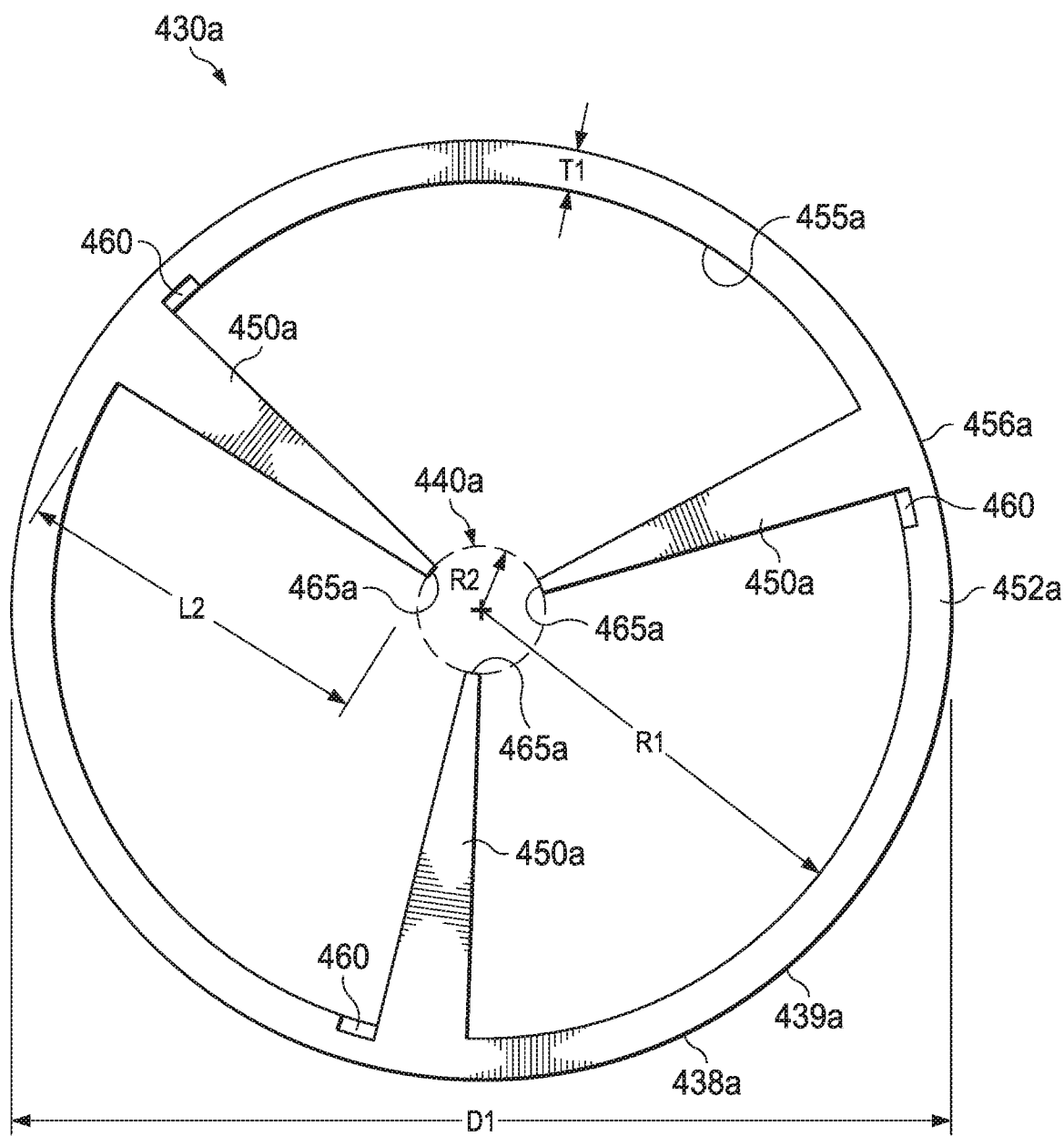
FIG. 5B illustrates a top view of the exemplary support member shown in FIG. 5A according to one embodiment of the present disclosure.

FIG. 5A illustrates a perspective view of the support member 430a of the instrument guiding apparatus 400 shown in FIG. 4 according to one embodiment of the present disclosure. FIG. 5B illustrates a top view of the support member 430a (i.e., showing the distal end 452a) according to one embodiment of the present disclosure. The support member 430a is the proximal-most support member of the telescoping support assembly 410. In the pictured embodiment, the support member 430a is shaped as a hollow cylinder having a wall 438a, a central passageway 440a, and three flanges 450a extending inwards toward the radial center of the support member 430a. In particular, the three flanges 450a extend from the wall 438a toward the radial center of the support member 430a to define the central passageway 440a. In other embodiments, the support member 430a may have any of a variety of other shapes, including without limitation, cuboid, ovoid, prismatic, or rhomboid. The support member 430a includes a height H1 extending from a proximal end 451a to a distal end 452a of the support member 430a. In the pictured embodiments, the flanges 450a share the same height H1. In other embodiments, the flanges 450a may include a flange height that is less than or greater than the height H1. The height H1 may range from 1.0 mm to 100 mm. In some embodiments, the height H1 measures 20 mm. Other heights are contemplated.

As shown in FIGS. 5A and 5B, the wall 438a of the support member 430a comprises a complete cylindrical ring 439a having a diameter D1, an inner surface 455a, and an outer surface 456a. The diameter D1 may range from 5.0 mm to 50 mm. In some embodiments, the diameter D1 measures 30 mm. Other diameters are contemplated. The wall 438a has a wall thickness T1. In the pictured embodiment, the wall thickness T1 is approximately the same around the entire support member 430a. In other embodiments, the wall thickness T1 may vary at different radial locations around the wall 438a. The thickness T1 may range from 1.0 mm to 10.0 mm. In some embodiments, the wall thickness T1 measures 2.5 mm. Other thicknesses are contemplated. In the pictured embodiment, the inner surface 455a of the wall 438a includes at least two grooves 460. The grooves 460 can be sized to receive flanges of more distal support members 430 when the telescoping support assembly 410 is in a compressed configuration. The pictured grooves 460 may extend the height of the wall 438a. In some embodiments, the grooves 460 extend less than the entire height H1 of the wall 438a.

As best shown in FIG. 5B, the flanges 450a are shaped as generally wedge-shaped, prism-like projections that extend perpendicularly from the inner surface 455a of the wall 438a towards the center of the support member 430a. In some embodiments, the flanges may extend at different angles (e.g., at acute or obtuse angles) from the inner surface 455a. In the pictured embodiment, the flanges 450a taper from a wider base at the inner surface 455a towards a narrower flange tip 465a. In other embodiments, the flanges 450a may be shaped differently. For example, the flanges 450a may have more rounded (e.g., semicircular or elliptical) or more angular (e.g., rectangular or rhomboid) profiles. In some embodiments, the flange tips 465a are rounded or capped to guard against damage to the catheter 310 and to minimize friction between the catheter 310 and the support member 430a. In the pictured embodiment, the flanges comprise elongate wedges that taper from a wide base at the inner surface of the ring 439a to the narrow flange tips 465a, which define a circumferential boundary of the central passageway 440a. The flanges 450a are evenly spaced around the circumference of the inner surface 455a of the wall 438a. In the pictured embodiment, the flanges 450a are spaced apart from adjacent flanges by approximately 120 degrees. In other embodiments, the flanges 450a may be unevenly spaced from one another, and the angular relationship between them may change. In the pictured embodiment, the support member 430a includes three flanges 450a. In other embodiments, the support member 430a may include more flanges. The flanges 450a are positioned at opposing angles such that the flange tips 465a are disposed to support the catheter 310 as it passes through the central passageway 40a of the support member 430a. The flanges 450a include a length L2 extending from the inner surface 455a to the flange tip 465a that measures less than an inner radius R1 of the support member 430a. Thus, the flanges tips 465a define the central passageway 440a, which comprises a cylindrical space running through the center of the support member 430a.

The central passageway 440a is sized to allow for the passage of the catheter 310 and includes a radius R2. In the pictured embodiment, the radii of the central passageways 440 of each of the support members 430 remains constant through the length of the telescoping support assembly 410. In other embodiments, the radius of the central passageways 440 of the individual support members 430 may be different.

Figure 6A:
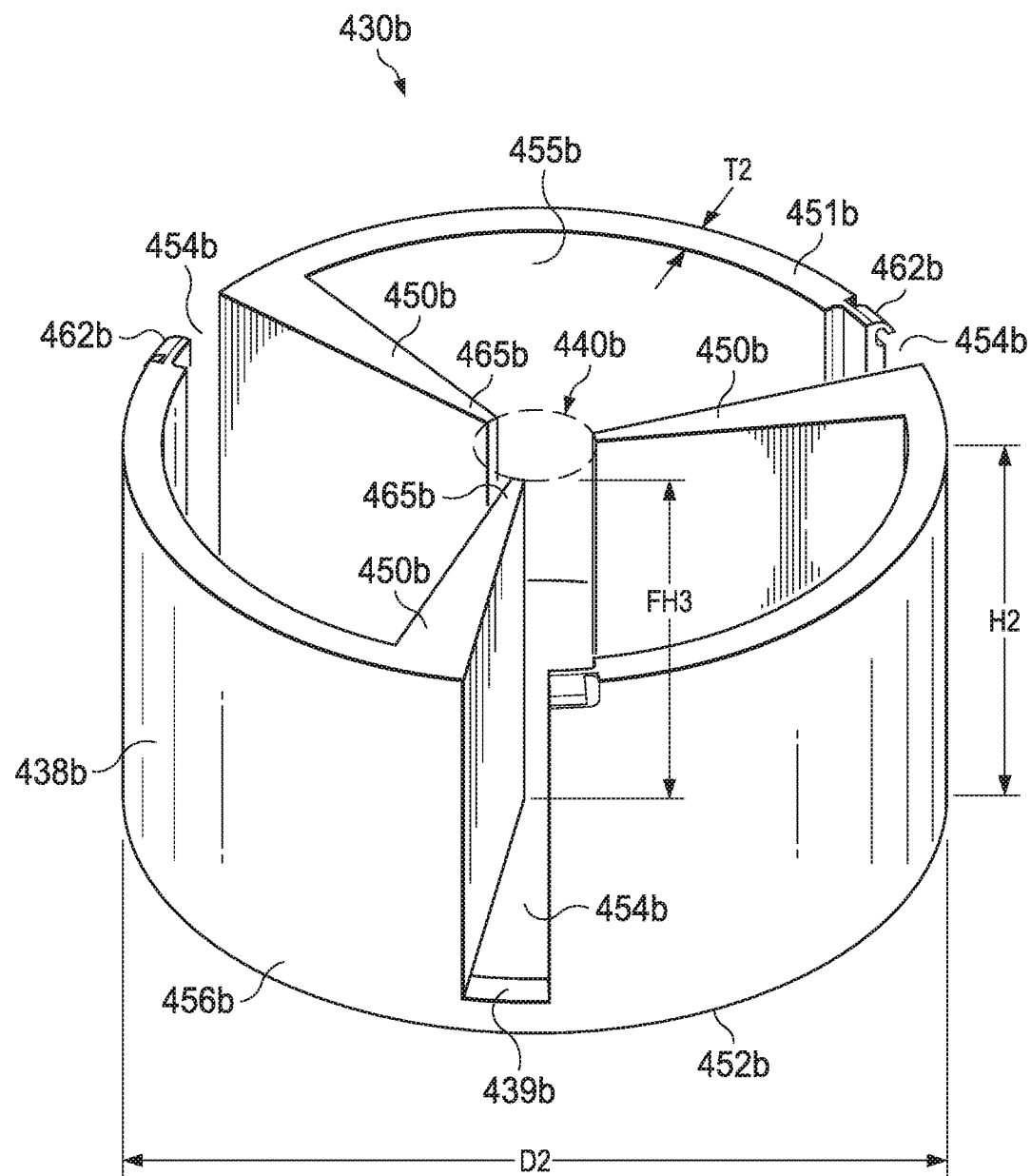
FIG. 6A illustrates a perspective view of another exemplary support member of the instrument guiding apparatus shown in FIG. 4 according to one embodiment of the present disclosure.
Figure 6B:
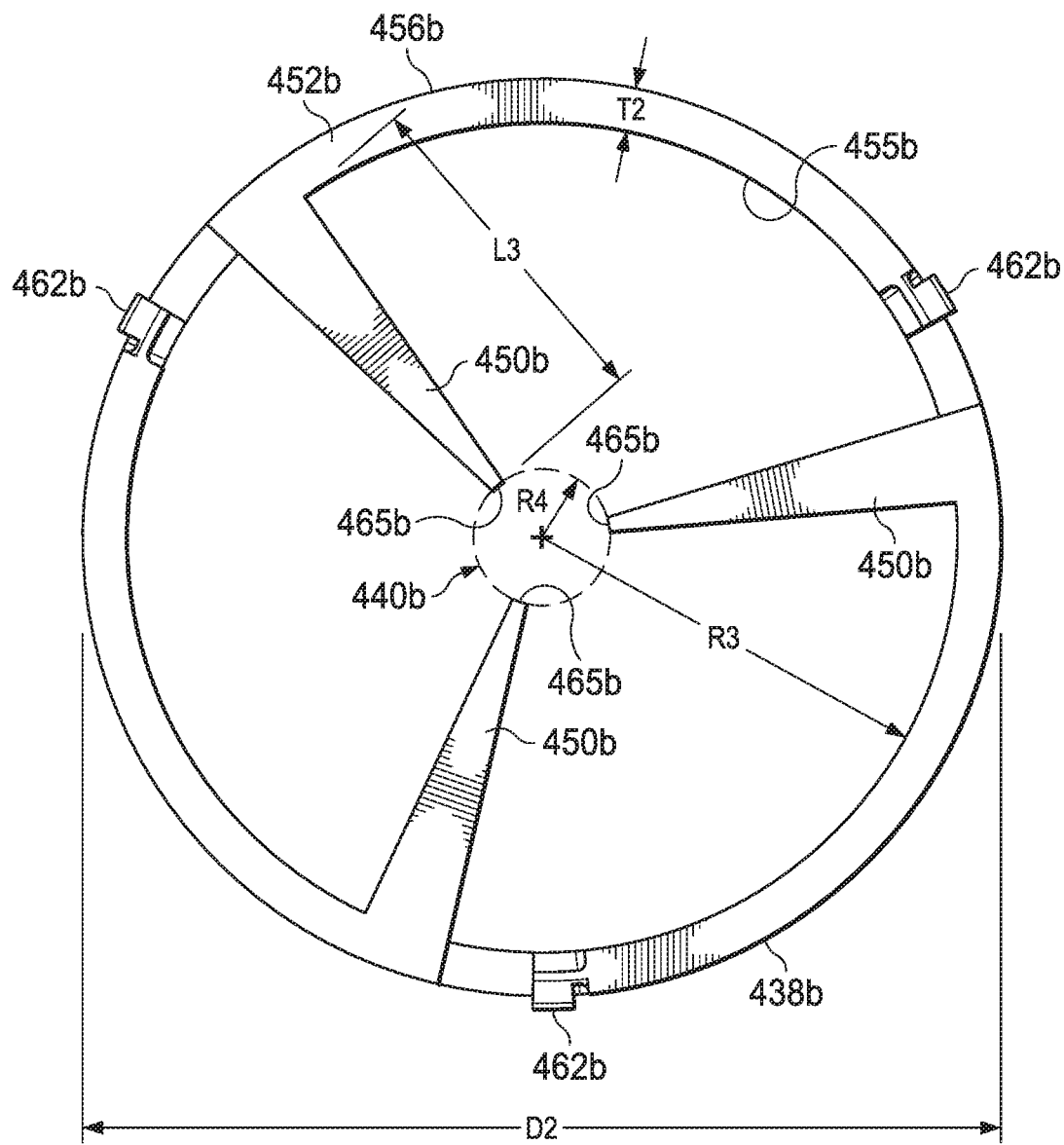
FIG. 6B illustrates a top view of the exemplary support member shown in FIG. 6A according to one embodiment of the present disclosure.

FIG. 6A illustrates a perspective view of the support member 430b of the instrument guiding apparatus 400 shown in FIG. 4 according to one embodiment of the present disclosure. FIG. 6B illustrates a top view of the support member 430b (i.e., showing a distal end 452b) according to one embodiment of the present disclosure. The support member 430b is adjacent to the proximal-most support member 430a of the telescoping support assembly 410. The support member 430b is substantially similar to the support member 430a except for the differences described herein. In the pictured embodiment, the support member 430b is shaped as a hollow cylinder having a wall 438b rising from a distal ring 439b, a central passageway 440b, and three flanges 450b extending inwards toward the radial center of the support member 430b. In particular, the three flanges 450b extend into the center of the support member 430b to define the central passageway 440b. In other embodiments, the support member 430b may have any of a variety of other shapes, including without limitation, cuboid, ovoid, prismatic, or rhomboid. The support member 430b includes a height H2 extending from a proximal end 451b to a distal end 452b of the support member 430a. In the pictured embodiments, the flanges 450b include a flange height FH3 that is slightly shorter than the height H2 of the support member 430b. In other embodiments, the flanges 450b may be the same length or shorter than the height H2. The height H2 may range from 10.0 mm to 100 mm. In some embodiments, the height H2 measures 20.0 mm. The flange height FH3 may range from 8.0 mm to 98.0 mm. In some embodiments, the flange height FH3 measures 17.0 mm. Other heights are contemplated.

As shown in FIG. 6B, the wall 438b of the support member 430b comprises an interrupted cylindrical wall having a diameter D2, an inner surface 455b, and an outer surface 456b. The diameter D2 is less than the diameter D1 of the support member 430a. Each support member 430 includes a diameter that is less than the diameter of the more proximal support members 430. The diameter D2 may range from 5.0 mm to 50.0 mm. In some embodiments, the diameter D2 measures 30.0 mm. Other diameters are contemplated. The wall 438b has a wall thickness T2. In the pictured embodiment, the wall thickness T2 is approximately the same around the entire support member 430b. In other embodiments, the wall thickness T2 may vary at different radial locations around the wall 438b. The thickness T2 may range from 1.0 mm to 10.0 mm. In some embodiments, the wall thickness T2 measures 2.5 mm. Other thicknesses are contemplated.

In the pictured embodiment, the inner surface 455b of the wall 438b includes at least two coupling members 462b. The coupling members 462b are sized and shaped to mate with coupling members of proximally adjacent support members 430 of the telescoping support assembly 410. In the pictured embodiment, the coupling members 462b are shaped as hook-like fasteners. Other types of coupling fasteners are contemplated, including mating ledges, protrusions, and recesses. The pictured coupling members 462b are disposed on the proximal end 451b of the wall 438b. In various embodiments, the coupling members 462b may be disposed on the outer surface 456b or the inner surface 455b. Although not pictured, each of the more distal support members 430 may share similar type of coupling mechanisms to link adjacent support members 430 and to prevent them from separating when the telescoping support assembly 410 assumes an extended configuration. For example, each centrally located coupling member 430b-i may include proximal coupling members adjacent the proximal end of the support member and distal coupling members adjacent the distal end of the support member. The proximal coupling members of each support member 430 may couple with the distal coupling members of the proximally adjacent support member 430.

Figure 10:
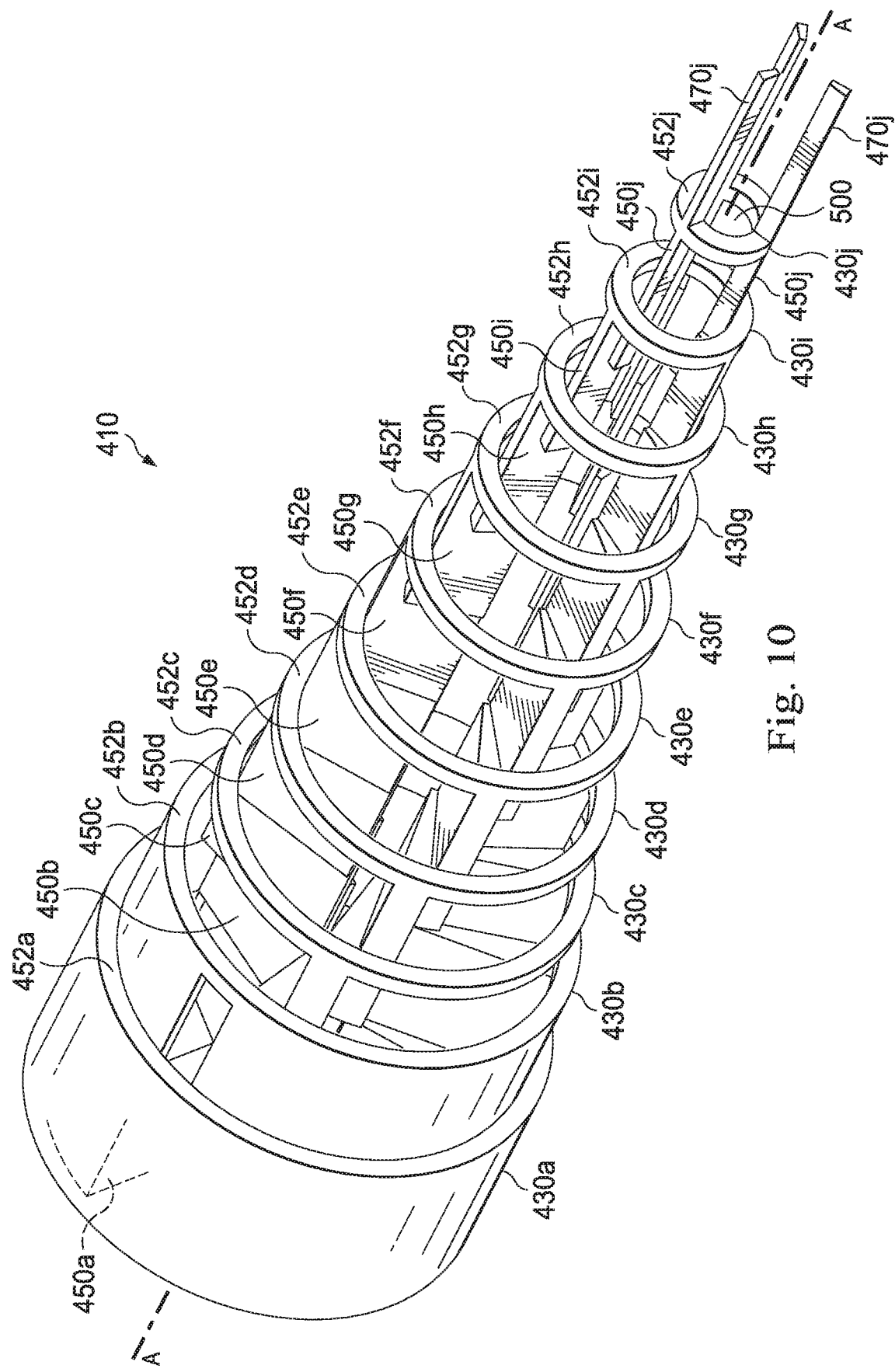
FIG. 10 illustrates a perspective view of an exemplary telescoping support assembly shown in FIG. 4 in an expanded configuration.

The flanges 450b are shaped as generally wedge-shaped, prism-like projections that extend from the inner surface 455b of the wall 438b towards the radial center of the support member 430b. The wall 438b is broken into three discrete sections by three apertures 454b. Each of the three flanges 450b extend from a separate section of the wall 438b. The proximal, circumferential part of the wall 438b forms the distal ring 439b. When the telescoping support member 410 transitions into a compressed configuration, the apertures 454b receive the flanges 450a of the proximally adjacent support member 430a, as shown in FIG. 10.

The flanges 450b are substantially similar to the flanges 450a described above, and taper from a wider base at the inner surface 455b towards a narrower flange tip 465b. In other embodiments, the flanges 450b may be shaped differently. For example, the flanges 450b may have more rounded (e.g., semicircular or elliptical) or more angular (e.g., rectangular or rhomboid) profiles. In some embodiments, the flange tips 465b are rounded or capped to guard against damage to the catheter 310 and to minimize friction between the catheter 310 and the support member 430b. The flanges 450b are evenly spaced around the circumference of the inner surface 455b of the wall 438b. In the pictured embodiment, the flanges 450b are spaced apart from adjacent flanges by approximately 120 degrees. In other embodiments, the flanges 450b may be unevenly spaced from one another, and the angular relationship between them may change. However, the angular relationship between the flanges 450 of one support member 430 generally match the angular relationship between the flanges 450 of each of the remaining support members 430, thereby facilitating the nesting of the flanges 450 within adjacent support members 430.

In the pictured embodiment, the support member 430b includes three flanges 450b. In other embodiments, the support member 430b may include more or less flanges. The flanges 450b are positioned at opposing angles such that the flange tips 465a are disposed to support the catheter 310 as it passes through the central passageway 40a of the support member 430b. The flanges 450b include a flange length L3 extending from the inner surface 455b to the flange tip 465a that measures less than an inner radius R3 of the support member 430b. Thus, the flanges tips 465a define the central passageway 440b, which comprises a cylindrical space running through the center of the support member 430b. The inner radius R3 of the support member 430b measures less than the inner radius R1 of the larger support member 430a, and the flange length L3 of the flanges 450b measures less than the flange length L2 of the flanges 450a of the larger support member 430a. To facilitate the nesting action of the telescoping support assembly 410, each subsequent distal support member 430 includes shorter flanges 450 and smaller inner radii than the proximally adjacent support member 430.

The central passageway 440b is sized to allow for the passage of the catheter 310 and includes a radius R4. As mentioned above, in the pictured embodiment, the radii (i.e., radii R2 and R4) of the central passageways 440 of each of the support members 430 remains constant through the length of the telescoping support assembly 410. A constant radius for the central passageways 440 facilitates consistent lateral support along the length of the medical instrument passing through the support members 430. In other embodiments, as mentioned above, the radii of the central passageways 440 of the individual support members 430 may be different.

Figure 7:
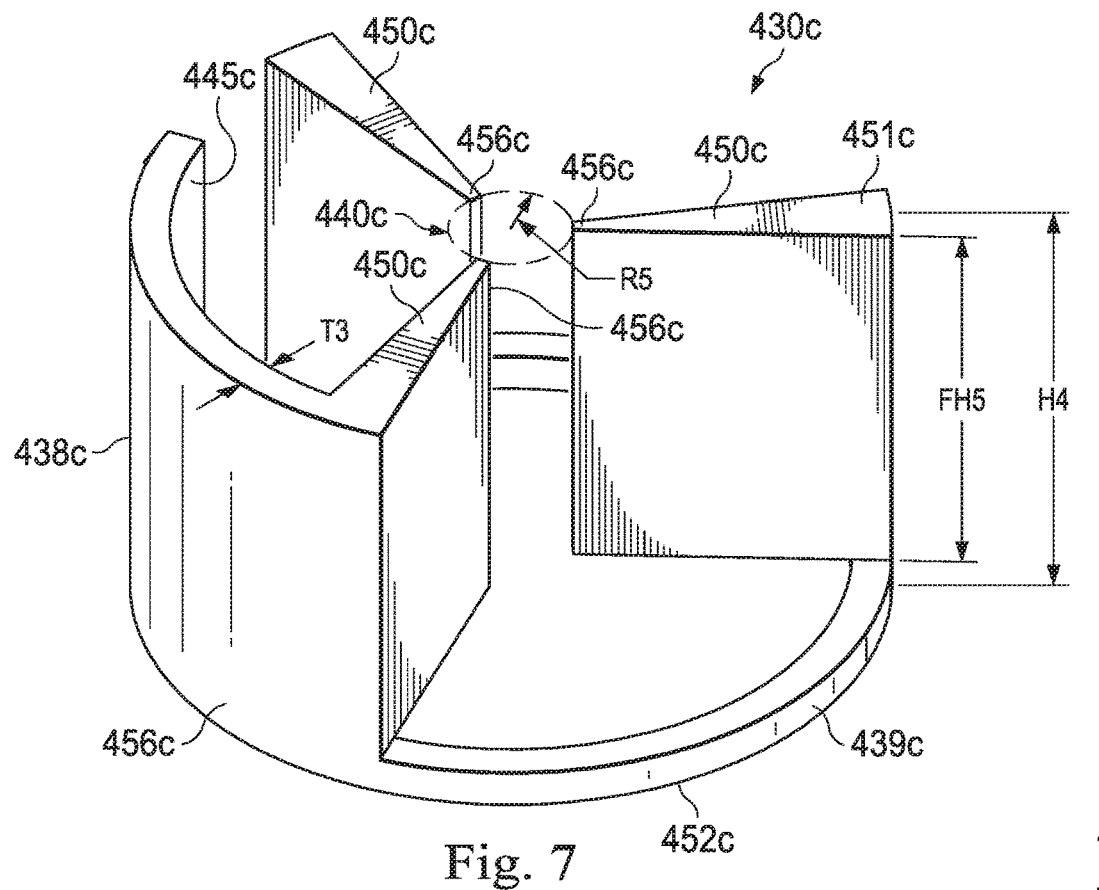
FIG. 7 illustrates a perspective view of another exemplary support member of the instrument guiding apparatus shown in FIG. 4 according to one embodiment of the present disclosure.

FIG. 7 illustrates a perspective view of the support member 430c of the instrument guiding apparatus 400 shown in FIG. 4 according to one embodiment of the present disclosure. The support member 430c is substantially similar to the support member 430b except for the differences described herein. In the pictured embodiment, the support member 430b has a generally cylindrical profile with an wall 438c rising from a distal ring 439c, a central passageway 440c, and three flanges 450c extending inwards toward the center of the support member 430c. In particular, the three flanges 450c extend toward the radial center of the support member 430c to define the central passageway 440c. The support member 430c includes a height H4 extending from a proximal end 451c to a distal end 452c of the support member 430c.

In this embodiment, except for the distal-most support member 430j, the heights of each support member 430 are the same. For example, the height H4 measures the same as the heights of the remaining support members. In other embodiments, the heights of the individual support members 430 may vary. Each flange 450c includes a flange height FH5 that measures less than the height H4 of the support member 430c. In the pictured embodiment, the flanges 450 of each support member 430 include shorter flange heights than the overall heights of their respective support member 430. This allows for the support members 430 to nest completely within each other when the telescoping support assembly 410 assumes a compressed configuration, as shown in FIGS. 13 and 14.

As shown in FIG. 7, the wall 438c of the support member 430c comprises an arcuate wall having an inner surface 455c and an outer surface 456c. The wall 438c has a wall thickness T3. In the pictured embodiment, the wall thickness T2 is approximately the same as the thickness T2 of the support member 430b. In other embodiments, the wall thickness of different support members 430 may vary. The thickness T3 may range from 1.0 mm to 10.0 mm. In some embodiments, the wall thickness T3 measures 2.5 mm. Other thicknesses are contemplated.

The flanges 450c are shaped as generally wedge-shaped, prism-like projections that extend from the ring 439c towards the center of the support member 430b. One flange 450c is a continuous extension from the inner surface 455c of the wall 438b. In the pictured embodiment, the ring 439c is continuous with the proximal part of the wall 438c. When the telescoping support member 410 transitions into a compressed configuration, apertures 454c between the wall 438c and the flanges 450c receive the flanges 450a, 450b of the proximal support members 430a, 430b, respectively, as shown in FIG. 10.

The flanges 450c are positioned at opposing angles such that flange tips 465c are disposed to support the catheter 310 as it passes through the central passageway 440c of the support member 430c. The central passageway 440c is sized to allow for the passage of the catheter 310 and includes a radius R5. As mentioned above, in the pictured embodiment, the radii of the central passageways 440 of each of the support members 430 remains constant through the length of the telescoping support assembly 410. In other embodiments, as mentioned above, the radius of the central passageways 440 of the individual support members 430 may be different.

Figure 8:
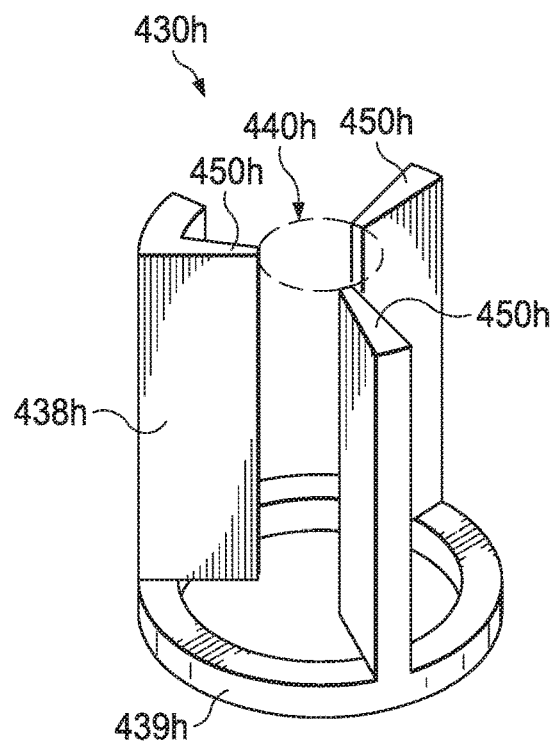
FIG. 8 illustrates a perspective view of another exemplary support member of the instrument guiding apparatus shown in FIG. 4 according to one embodiment of the present disclosure.

FIG. 8 illustrates a perspective view of the support member 430h of the instrument guiding apparatus 400 shown in FIG. 4 according to one embodiment of the present disclosure. The support member 430h is substantially similar to the support member 430c except for the differences described herein. In the pictured embodiment, the support member 430h has a generally cylindrical profile with an wall 438h rising from a distal ring 439h, a central passageway 440h, and three flanges 450h extending inwards toward the radial center of the support member 430h. One difference between the support member 430h and the support member 430c is that the wall 438h is smaller (i.e., has a smaller circumference or partial circumference C2) than the wall 438c. The outer walls 438 of the more distal support members 430 may include progressively smaller circumferential lengths. FIGS. 5-8 illustrate that the more distal support members 430 include progressively smaller overall diameters than their more proximal counterparts, and the outer walls 438 are proportionately smaller in accordance with those decreasing diameters, and FIG. 9 shows that the distal-most support member 430j lacks an wall altogether.

Figure 9:
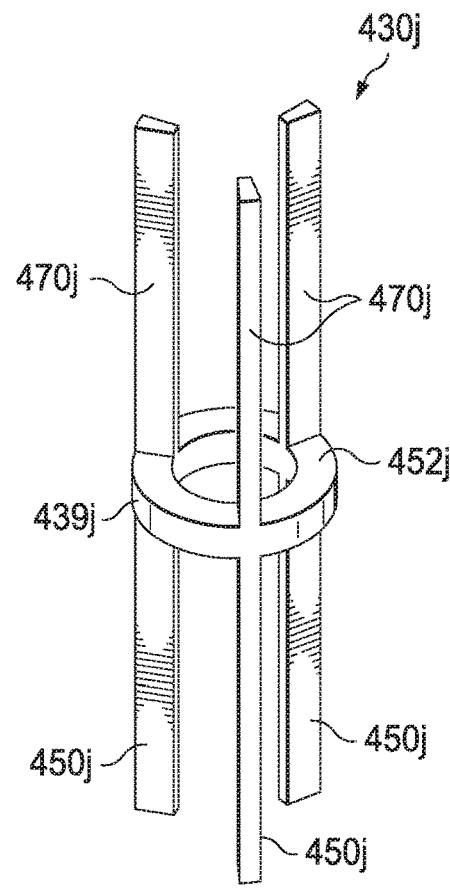
FIG. 9 illustrates a perspective view of another exemplary support member of the instrument guiding apparatus shown in FIG. 4 according to one embodiment of the present disclosure.

FIG. 9 illustrates a perspective view of the distal-most support member 430j of the instrument guiding apparatus 400 shown in FIG. 4 according to one embodiment of the present disclosure. The support member 430j is substantially similar to the support member 430h except for the differences described herein, including three flanges 450j. In particular, as mentioned above, the support member 430j lacks an outer wall, and includes three additional flanges 470 that extend distally past a distal end 452j. In some embodiments, another telescoping support assembly (i.e., a symmetric stack of support members) may be attached to the instrument guiding apparatus 400 at the additional flanges 470 to increase the overall length of the support assembly.

Figure 15:
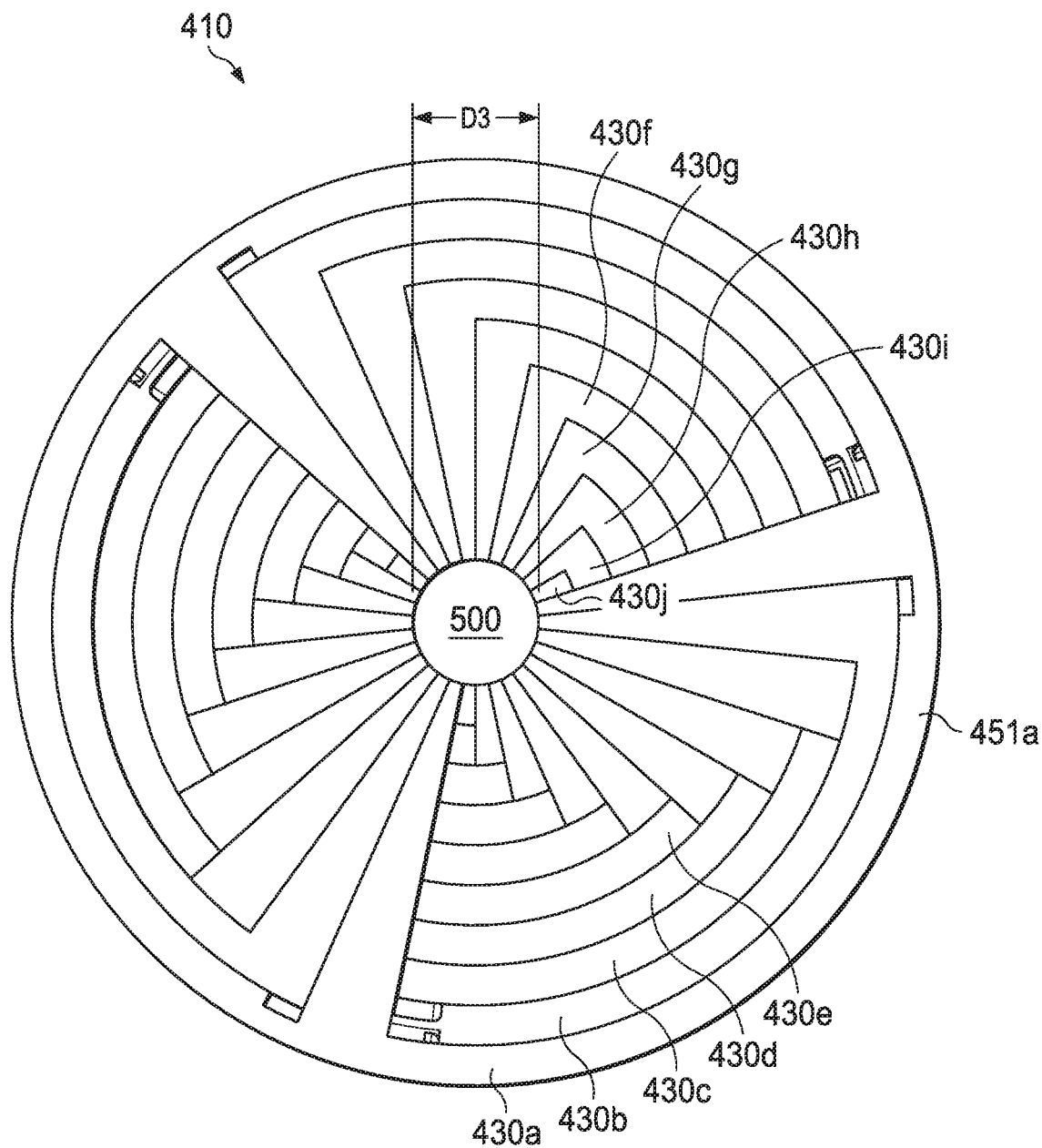
FIG. 15 illustrates a top view of the telescoping support assembly shown in FIG. 4 according to one embodiment of the present disclosure.

FIGS. 10-12 illustrate various perspective views of the telescoping support assembly 410 in an expanded configuration. FIG. 13 illustrates a perspective view (from the top) of the telescoping support assembly 410 in a compressed configuration according to one embodiment of the present disclosure. FIG. 14 illustrates a perspective view (from the bottom) of the telescoping support assembly 410 in a compressed configuration. FIG. 15 illustrates a top view of the telescoping support assembly 410 according to one embodiment of the present disclosure.

As shown in FIGS. 10-12, the support members 430 are linked in series in a telescoping arrangement. The support members 430 are linked to align the central passageways 440 of each support member 430 on the insertion axis A along the length of the telescoping support assembly 410, creating a continuous channel 500 running through the telescoping support assembly 410. When the telescoping support assembly 410 is collapsed in a compressed configuration, as shown in FIGS. 13-15, the support members 430 are nested snugly into one another, with each support member 430 nesting into the proximally adjacent support member 430 and the rings 439 of each support member 430b-j resting against the rings 439 of the adjacent support members 430 on either side. In contrast, as shown in FIGS. 10-12, when the telescoping support assembly 410 is spread out in an expanded configuration, the rings 439 of the support members 430 are spaced apart from each other.

The channel 500 is sized and shaped to permit the easy passage of the catheter 310 therethrough. As shown in FIG. 15, the channel 500 has a diameter D3 that is sized to accommodate the catheter 310. The diameter D3 may range from 1.0 mm to 20.0 mm. In some embodiments, the diameter D3 measures 3.0 mm. Other diameters are contemplated.

The flanges 450 of each individual support member 430 support almost the entire length of catheter 310 positioned within that particular support member. The short portion of the catheter 310 that is unsupported by the flanges 450 (i.e., at the level of the distal ring 439) is supported by the flanges 450 of the distally adjacent support member 430. Thus, instead of leaving the catheter 310 unsupported between the rings 439 of the support members 430, the flanges 450 of the telescoping support assembly 410 can support the entire exposed length of the catheter 310 when the telescoping support assembly 410 is in an expanded configuration. The support members are linked in a spiral fashion. The support members 430 are radially offset from one another such that the flanges 450 of each support member 430 can nest into each proximal support member 430. In particular, each support member 430 is radially offset from the immediately adjacent support member 430 to allow for the flanges 450 of neighboring support members 430 to contact and slide against each other as the telescoping support assembly 410 compresses and expands. Such an arrangement maximizes the lateral support available to the catheter (i.e., in the form of elongated flanges) while minimizing the compressed length of the telescoping support assembly 410. In some embodiments, the flanges 450 of adjacent support members 430 do not contact one another. For example, some embodiments may include support members 430 that are radially offset from one another by more degrees than occupied by the wider base of the flange (i.e., the arcuate distance occupied by the flange 450 on the circumference of the wall 438 or the ring 439).

The systems and methods of this disclosure are suitable for use with any flexible elongate device used within connected passageways such as in the connected bronchial passageways of the lung, as well as for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for any non-interventional or non-medical applications which require variable length support of a flexible or non-flexible elongate device, tool, or instrument. Any reference to medical or surgical instruments and medical or surgical methods herein is non-limiting. The systems, instruments, and methods described herein may be used for animals, human cadavers, animal cadavers, portions of human or animal anatomy, non-surgical diagnosis, as well as for industrial systems and general robotic or teleoperational systems.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus for guiding an elongated flexible instrument, the apparatus comprising:
   a telescoping support assembly including a proximal end, a distal end, and a plurality of support members extending along a longitudinal axis between the proximal end and the distal end, each of the plurality of support members comprising a ring having an inner surface, an outer surface, and at least one flange, the at least one flange of each of the plurality of support members extending from the inner surface of the ring to define a central passageway extending along the longitudinal axis and having a substantially constant width transverse to the longitudinal axis;
   wherein the central passageway is configured to receive the elongated flexible instrument; and
   wherein the telescoping support assembly is configured to selectively transition from a compressed configuration to an expanded configuration along the longitudinal axis while each support member of the plurality of support members is interlocked with at least one other support member of the plurality of support members, and is adapted to support the elongated flexible instrument as the elongated flexible instrument is advanced along the longitudinal axis.

2. The apparatus of claim 1, wherein an exposed length of the elongated flexible instrument is supported by the at least one flange.

3. The apparatus of claim 1, wherein the at least one flange of each of the plurality of support members extend at a perpendicular angle from the inner surface of the ring toward a radial center of the support member.

4. The apparatus of claim 1, wherein the at least one flange of each support member comprises an elongate wedge extending from the inner surface of the ring.

5. The apparatus of claim 4, wherein each of the elongate wedges taper from a wide base at the inner surface of the ring to a narrow flange tip.

6. The apparatus of claim 5, wherein the flange tip defines a circumferential boundary of the central passageway.

7. The apparatus of claim 1, wherein each of the plurality of support members includes at least three flanges including the at least one flange.

8. The apparatus of claim 1, wherein each of the plurality of support members further comprises a plurality of coupling members that selectively connect adjacent support members to each other by preventing the adjacent support members from disengaging when the telescoping support assembly assumes an expanded configuration.

9. The apparatus of claim 8, wherein each of the plurality of coupling members comprise a mating fastener, wherein a first set of coupling members is disposed on a distal end of a proximal support member and a second set of coupling members is disposed on a proximal end of a distally adjacent support member.

10. The apparatus of claim 1, wherein each of the plurality of support members are radially offset from one another such that the at least one flange of each support member can nest into each adjacent support member.

11. The apparatus of claim 10, wherein the at least one flange of at least one support member is configured to contact the at least one flange of at least one proximally adjacent support member and the at least one flange of at least one distally adjacent support member.

12. The apparatus of claim 1, further comprising at least one of:
a proximal coupler at the proximal end of the telescoping support assembly, the proximal coupler configured to couple the telescoping support assembly to an instrument interface portion; and
a distal coupler at the distal end of the telescoping support assembly, the distal coupler configured to couple the telescoping support assembly to a stabilizer.

13. The apparatus of claim 1, wherein each of the plurality of support members further comprises a wall, wherein the wall comprises the ring and is coupled to the at least one flange.

14. The apparatus of claim 13, wherein the wall comprises at least a portion of a cylinder.

15. A system, comprising:
an elongated flexible instrument; and
a telescoping support assembly including a proximal end, a distal end, and a plurality of support members extending along a longitudinal axis between the proximal end and the distal end, each of the plurality of support members comprising a ring including an inner surface, an outer surface, and at least one flange, the at least one flange extending from the inner surface of the ring to define a central passageway, wherein the central passageway is configured to receive the elongated flexible instrument such that the elongated flexible instrument occupies a majority of a volume of the central passageway in an expanded configuration, and wherein the telescoping support assembly is configured to selectively transition from a compressed configuration to the expanded configuration along the longitudinal axis, while each of the plurality of support members is interlocked with at least one other support member, and is adapted to support the elongated flexible instrument as the elongated flexible instrument is advanced along the longitudinal axis.

16. The system of claim 15, wherein the elongated flexible instrument is supported along an entire length of the telescoping support assembly by the plurality of support members.

17. The system of claim 15, wherein the telescoping support assembly is configured to selectively transition from the compressed configuration to the expanded configuration as the elongated flexible instrument is inserted into the telescoping support assembly.

18. The system of claim 15, wherein the telescoping support assembly is configured to selectively transition from the expanded configuration to the compressed configuration as the elongated flexible instrument is advanced into a patient anatomy.

19. The system of claim 15, wherein a first support member of the plurality of support members comprises a first plurality of flanges, wherein a second support member of the plurality of support members comprises a second plurality of flanges, and wherein an angular relationship between adjacent flanges of the first plurality of flanges is equal to an angular relationship between adjacent flanges of the second plurality of flanges.

20. The system of claim 15, further comprising:
an anchor couplable to a distal end of the telescoping support assembly, the anchor configured to be disposed between the telescoping support assembly and a patient anatomy and configured to stabilize the telescoping support assembly.

21. The apparatus of claim 1, wherein the at least one flange of each of the plurality of support members extends a distance from the inner surface of the ring that is different than a distance the at least one flange of an adjacent support member extends from the inner surface of the ring of the adjacent support member.

22. The system of claim 15, wherein the ring of each of the plurality of support members has a diameter that is different than a diameter of the ring of each other support member.

* * * * *